US005809999A

United States Patent [19]

Lang

[11] Patent Number: 5,809,999

[45] Date of Patent: Sep. 22, 1998

[54] METHOD AND APPARATUS FOR SUPPLYING BREATHABLE GAS IN EMERGENCY OXYGEN SYSTEMS, ESPECIALLY IN AN AIRCRAFT

[75] Inventor: Stephan Lang, Neu Wulmstorf, Germany

[73] Assignee: Daimler-Benz Aerospace Airbus GmbH, Hamburg, Germany

[21] Appl. No.: 705,531

[22] Filed: Aug. 29, 1996

[30] Foreign Application Priority Data

Aug. 30, 1995 [DE] Germany ........................ 195 31 916.8

[51] Int. Cl.$^6$ ........................ A61M 15/00; A61M 16/00; A62B 7/00; A62B 9/00

[52] U.S. Cl. ................................ 128/200.24; 128/201.24; 128/204.15; 128/204.18; 128/206.21; 244/118.5

[58] Field of Search ......................... 128/200.24, 201.24, 128/204.15, 204, 18, 206.21, 204.22; 244/118.5

[56] References Cited

U.S. PATENT DOCUMENTS

| | | | |
|---|---|---|---|
| 4,394,861 | 7/1983 | Sciortino | 128/205.25 |
| 4,428,372 | 1/1984 | Beysel et al. | 128/202.26 |
| 4,568,522 | 2/1986 | Corbett | 422/186 |
| 5,071,453 | 12/1991 | Hradek et al. | 55/21 |
| 5,357,949 | 10/1994 | Bertheau et al. . | |

FOREIGN PATENT DOCUMENTS

| | | |
|---|---|---|
| 1170792 | 5/1964 | Germany . |
| 4104007 | 8/1991 | Germany . |

*Primary Examiner*—V. Millin
*Assistant Examiner*—Dinh X. Nguyen
*Attorney, Agent, or Firm*—W. G. Fasse; W. F. Fasse

[57] ABSTRACT

In an emergency oxygen supply system of an aircraft equipped with a pressurized cabin, breathable gas is supplied by a gas generator (1) for generating an oxygen-enriched gas either from the ambient air, or from air tapped from the engine, or from fresh water. The generator may also generate practically pure oxygen. A mixed gas is produced in a mixing unit (14) from the breathable gas and oxygen as needed especially in short duration transition periods to meet official regulations. The oxygen partial pressure in the mixed gas is varied or controlled depending on the cabin pressure. The breathable gas is fed in a constant mass flow through an on-board distribution network to the breathing masks connected to the network. Selectable masks for the crew may receive pure oxygen while most other masks for the passengers receive mixed gas having an adequate oxygen content.

22 Claims, 2 Drawing Sheets

FIG. 1

METHOD AND APPARATUS FOR SUPPLYING BREATHABLE GAS IN EMERGENCY OXYGEN SYSTEMS, ESPECIALLY IN AN AIRCRAFT

FIELD OF THE INVENTION

The invention relates to a method for providing breathable gas in emergency oxygen systems for aircraft, particularly passenger aircraft equipped with a pressurized cabin. A breathable gas mixture is released through an on-board distribution network with breathing masks attached to the network. The invention also relates to an apparatus for implementing such a method.

BACKGROUND INFORMATION

Emergency oxygen systems in aircraft ensure in an emergency a supply of breathable oxygen through oxygen or breathing masks to the crew and the passengers. Such aircraft are equipped with a pressurized cabin and the emergency system responds to a suddenly occurring pressure drop in the pressurized cabin. The breathable oxygen is delivered to the breathing masks essentially according to two conventional methods. In the first conventional method oxygen is generated in a decentralized system by producing oxygen from solid matter in respective generators at the points of delivery to the crew and passengers. In the second conventional method, central oxygen reserves are provided in high pressure tanks, whereby the breathable oxygen is distributed to the individual consumers by a low pressure pipeline system and the oxygen flow rate is regulated either by a centralized or decentralized control system.

With both of these conventional methods, almost pure oxygen gas with an oxygen content of about 99.5% is delivered to the points of consumption, i.e. to the breathing masks, whereby the amount of oxygen that is delivered is regulated in the form of a mass flow rate control as a function of the cabin pressure. The oxygen is then mixed in the individual breathing masks with the ambient air in a way that maintains a partial pressure of oxygen in the mixture that is adequate for the consumers according to the latest aviation knowledge.

German Patent Publication DE AS 1,170,792 (Snowman et al.) discloses a device in which compressed air from compressors arranged in the aircraft is mixed in a mixing unit with compressed oxygen. The compressed oxygen and air are mixed at a ratio that is a function of the ambient air pressure and that maintains the required oxygen partial pressure. The apparatus disclosed by Snowman et al., however, serves exclusively to provide breathable air for pressurized cabins and high altitude breathing equipment. Such systems have not been considered heretofore for use in emergency oxygen supply equipment in passenger aircraft.

German Patent Publication DE 4,104,007 A1 (Harral et al.) discloses a computer controlled oxygen supply system for crew and passengers in a passenger aircraft. Gas containing at least a 90% oxygen concentration is produced and stored in a molecular sieve oxygen concentrator (11) connected to a monitor (35) and to a compressor (17) that delivers the high oxygen concentration gas to storage tanks (22) for the crew and storage tanks (23) for the passengers. The monitor (35) assures that the oxygen concentration is maintained.

U.S. Patent Publication 5,337,949 (Bertheau et al.) discloses an oxygen supply system for protecting aircraft passengers when the cabin should become depressurized at high altitudes. The delivery of pressurized oxygen takes place at different pressures depending on the altitude.

The disadvantages of these known methods lie on the one hand in a comparatively high risk potential for fire and explosions due to the use of practically pure oxygen. On the other hand the need for a relatively extensive control system for regulating the flow rate of the oxygen as a function of the current cabin pressure, i.e. as a function of the respective altitude, is a drawback based on weight and expense considerations.

OBJECTS OF THE INVENTION

In view of the above it is the aim of the invention to achieve the following objects singly or in combination:

- to provide a method for supplying a breathable gas mixture with an adequate or regulation prescribed partial pressure of oxygen for the consumers of the breathable air when a pressure drop occurs in a pressurized cabin, thereby avoiding using pure oxygen whenever possible;
- to utilize the nitrogen produced by the present system simultaneously with the breathable gas production, for practical purposes, e.g. to reduce the explosion danger or to recover energy used for the generation of breathable gas;
- to reduce to a minimum the potential risk of fire and explosions, which inherently exists when practically pure oxygen is used in such emergency oxygen systems;
- to simplify the control system for regulating or controlling the oxygen partial pressure in the breathable gas and thus, to reduce the cost of the system;
- to construct the present system so that it is less sensitive to damage by damaged aircraft components such as engine parts by simplifying devices needed for limiting leaks;
- to equip the present breathable gas generator with an extra high pressure outlet for gas having a high oxygen concentration for covering the peak oxygen requirements when an aircraft is in its first phase of an emergency descent; and
- to avoid the use of high pressure oxygen supply containers on board of the aircraft.

SUMMARY OF THE INVENTION

The above objects have been achieved by the method according to the invention which provides an on-board supply of an oxygen enriched breathable mixed gas to be fed into a distribution network, wherein the oxygen partial pressure in the breathable mixed gas is regulated or controlled as a function of the cabin pressure and the breathable oxygen-enriched gas is delivered to oxygen or breathing masks at a constant mass flow rate.

The method according to the invention significantly reduces the risk potential for fire and explosions compared to conventional methods because the concentration of oxygen in the on-board distribution system of the aircraft is much lower according to the invention than in conventional methods. The invention takes advantage of the fact that pure oxygen is not required for maintaining life sustaining breathing conditions on board of an aircraft in an emergency.

Furthermore, the present objects have been achieved by an apparatus according to the invention characterized by the following features for carrying out the present method. At least one gas generator is controlled in response to cabin pressure, especially a cabin pressure drop. The gas generator is connected to a distribution network to which breathing masks are connected. The gas generator is equipped with at least one low pressure outlet for supplying a breathable gas to be mixed with oxygen and at least one high pressure outlet for supplying oxygen for the mixing. Both outlets are connected to at least one mixing unit that is controlled, preferably in closed loop fashion, by a central control unit for regulating the addition of oxygen to the breathable gas to form the breathable mixed gas. The central control unit is equipped with a sensor for detecting the cabin pressure to provide a respective control signal for starting the system. Further, the mixing unit is equipped with a sensor for the oxygen partial pressure to provide a mixing control signal.

The structure of the present distribution system has been substantially simplified because closure valves that are conventionally required for limiting damage or rather limiting leakage by a so-called "engine burst protection", have been eliminated. Conventionally, it is necessary to protect the emergency oxygen supply against leaks caused by engine fragments that may fly about when an engine damage occurred, to prevent a greater oxygen leakage. The invention has replaced conventional leakage limiting devices by comparatively simple elements for limiting leaks. This is possible because the risk potential is significantly reduced, due to the substantially lower concentration of oxygen compared to conventional methods. At the same time, this simplification leads to an improved reliability of the present system and to a reduction in the required maintenance work. Furthermore, according to the invention, the mass flow of the emergency breathable mixed gas supply system is regulated or controlled instead of controlling the oxygen flow rate as a function of the cabin pressure. Regulating the mass flow of a lower oxygen content mixed gas that is hardly explosive is simpler than regulating the flow rate of essentially pure oxygen that can be highly explosive, whereby the reliability of the system is further improved and maintenance work has been further reduced.

The method according to the invention is particularly suitable to be practiced in connection with one or more gas generator units that produce the required breathable gas mixture directly in the aircraft.

In a preferred embodiment of the invention, the breathable gas to be enriched with oxygen in the aircraft can be generated in several ways from the ambient air, or from tap air drawn off from the engine whereby a separation process using molecular sieves or selectively functioning membranes is used for the present purposes. Instead of the above production possibilities, electrolysis of fresh water that is carried on board the aircraft may be used to produce the breathable gas. The production of an oxygen-enriched breathable mixed gas on board has several advantages compared to using pure oxygen. The safety risks involved with storing substantially pure oxygen are greatly reduced, since it is not necessary to maintain oxygen reserves in high pressure tanks. Further, the maintenance time and effort are reduced while the period of time that the supply lasts is substantially extended.

In order to guarantee an adequate supply of oxygen during the start-up phase of the present gas generation equipment after a sudden drop in pressure in the cabin, and to cover the peak demand for oxygen that occurs in the initial phase of an emergency descent of an aircraft, it is preferable according to the invention to provide a certain supply of gas with a high oxygen concentration. However, the volume of this high oxygen concentration gas is substantially smaller than conventional requirements. A preferred embodiment of the invention uses the gas generation equipment for this purpose, whereby the present gas generator has a low pressure breathable gas outlet and a high pressure outlet for providing gas with a high oxygen concentration. This feature provides the advantage that the same gas generator can be used for filling oxygen storage tanks that have a substantially smaller volume than is conventionally required.

In connection with the use of oxygen generating units it is possible to remain at higher altitudes for an extended period of time, even after a decompression of the pressurized cabin has occurred, thereby achieving a substantially lower fuel consumption or a correspondingly greater distance.

Another advantage achieved according to the invention is seen in that the nitrogen that is a by-product when the breathable gas is generated by a separation process using ambient air or air tapped from the engines, can be beneficially used. This nitrogen can be used either to flood empty volume portions of the fuel tanks, thereby reducing the danger of explosion or, by utilizing the pressure difference between the gas generating system and the environment, can be applied to drive a turbine to recover a portion of the energy used to generate the breathable gas.

BRIEF DESCRIPTION OF THE DRAWING

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
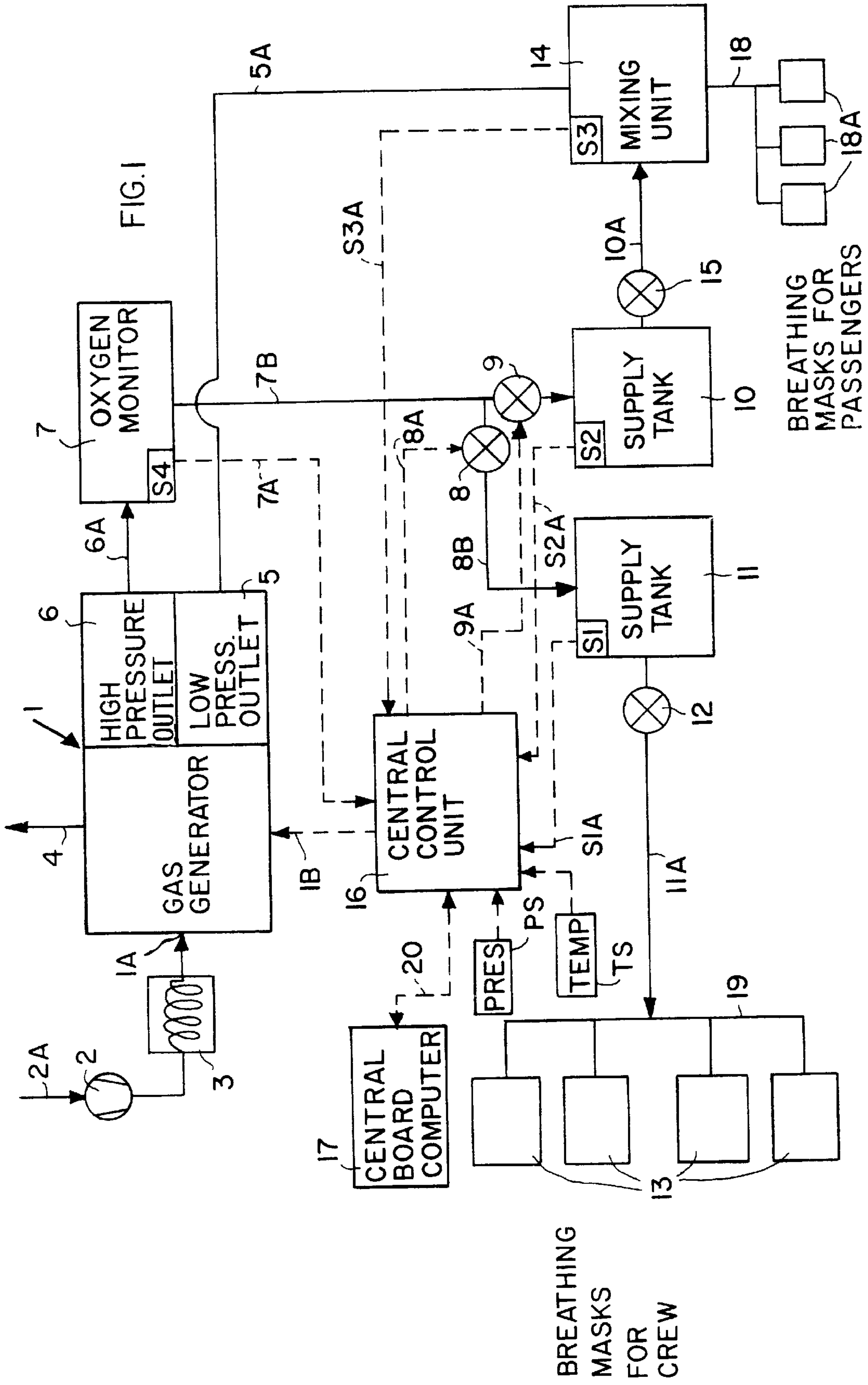
FIG. 1 shows schematically a block diagram of the present system for supplying a breathable mixed gas in an emergency caused by a pressure drop in an aircraft cabin.

The present system comprises a gas generator 1 that receives at its inlet 1A the raw material for generating a breathable gas. Several different supplies may be used. FIG. 1 shows the supply of fresh or ambient air 2A to the intake of a compressor 2 connected with its compressor outlet through a cooler 3 which is connected to the generator inlet 1A.

Figure 5:
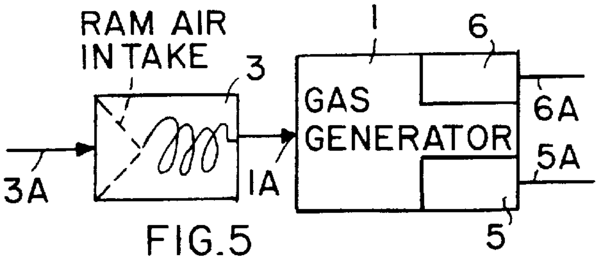
FIG. 5 shows an air cooler for raw air used in a breathable gas generator of the present system.

FIG. 5 shows a different embodiment without the compressor 2. Here, ambient air is compressed by a correspondingly constructed air intake, referred to as "ram air" intake shown in dashed lines in FIG. 5. The ram air intake feeds air through the cooler 3 to the generator inlet 1A. Instead of ambient air, air tapped from an engine not shown can be fed to the inlet 3A of the cooler 3. This tap air can be directly fed through the cooler 3 into the gas generator 1, without passing through a compressor.

Figure 6:
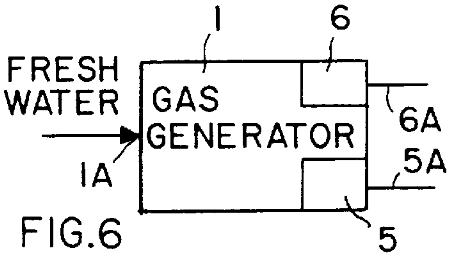
FIG. 6 shows schematically a fresh water intake of a gas generator producing a breathable gas by electrolytic decomposition of water.

FIG. 6 illustrates the possibility of using, in an emergency, fresh water as the starting material for the generation of breathable gas by electrolysis. Drinking water may be used for this purpose. Equipment for the decomposition of water by electrolysis is as such known in the art. As an alternative, extra fresh water may be carried on board the aircraft for this purpose.

Referring further to FIG. 1, the gas generator 1 is equipped with the necessary devices for producing from the supplied air a breathable gas having a higher concentration of oxygen than the incoming air. The concentration of oxygen can be increased by using the capability of a molecular sieve or by using selectively permeable membrane modules that have a preferential separating capability for oxygen. So-called electrochemical membranes can be used for this purpose, whereby oxygen ions are transported by an electrical field through a ceramic membrane. Downstream of the membrane, the oxygen ions are de-ionized again.

The gas generator 1 comprises, in addition to an exhaust 4 for discharging exhaust gas, a low pressure outlet 5 for delivering a breathable gas that has been enriched with oxygen, and a high pressure outlet 6 for delivering a gas component having a high oxygen content so that this component is practically pure oxygen under higher pressure than the gas from the low pressure outlet 5. The low pressure breathable gas outlet 5 is connected through a gas conduit 5A to a mixing unit 14 to be described in more detail below.

The high pressure outlet 6 is connected through a gas conduit 6A to an oxygen monitor 7 having an oxygen sensor S4 providing an oxygen characteristic representing signal on an electrical conductor 7A connecting the monitor 7 to a central control unit 16 which in turn is connected through a data bus 20 to a central on-board computer 17. A gas conduit 7B connects to monitor 7 through two shut-off valves 8 and 9 to two oxygen supply or storage tanks 10 and 11. The first tank 10 is provided for supplying the passengers. The second tank 11 is provided for supplying the cockpit crew. According to the embodiment shown here, the cockpit crew is supplied exclusively with pure oxygen is that is stored in the tank 11 provided with a sensor S1 connected through an electrical conductor S1A to the central control unit 16. The oxygen is fed to the crew members through a pressure reducing valve 12 in a gas conduit 11A and breathing masks 13 in which this oxygen is mixed with ambient air in a conventional manner or is provided as pure oxygen.

Incidentally, full line connections 5A, 6A, 7B, 8B, 10A, 11A, 18, 19 are gas conduits. Dashed line connections 1B, 7A, S1A, S2A, S3A, 8A, 9A, and 20 are electrical conductor connections for transmission of electrical signals including control signals.

The above mentioned mixing unit 14 is provided for supplying the passengers with a breathable mixed gas that has an oxygen content sufficient to meet airline regulations. The mixing unit 14 is connected preferably directly through gas conductor 5A to the low pressure outlet 5 of the generator 1. Unit 14 is also connected through a gas conduit 10A and a pressure reducing valve 15 to the oxygen supply tank 10. The mixing unit 14 includes a sensor S3 for ascertaining the oxygen partial pressure in the mixing unit 14. A signal conductor S3A connects the sensor S3 to the central control unit 16. The two shut-off valves 8 and 9, and further sensors S1, S2 of the supply tanks 10 and 11 are connected to the central control unit 16 through respective conductors 8A, 9A, S1A, S2A. The control unit 16 is connected to a pressure sensor PS for sensing the cabin pressure and to a temperature sensor TS to simultaneously supply pressure and temperature parameters or signals to the central control unit 16. Based on the input signals and in accordance with a respective program stored in a memory of the central on-board computer 17, the central control unit provides the control signals for the valves 8, 9 and other system control signals.

FIG. 1 does not show the details of an emergency breathable gas distribution network 18 that is equipped with calibrated mass flow control valves 18B and breathing masks 18A for the passengers. The crew has separate breathing masks 13 connected through distribution conduits 11A, 19 and pressure reducing valve 12 to the oxygen supply tank 11.

Even prior to the occurrence of a possible pressure drop sensed by the sensor PS, for example at the start of a flight when there is no pressure drop, the supply containers 10 and 11 are filled from the high pressure outlet 6 of the gas generator 1 with practically pure, highly compressed oxygen. The two closure valves 8 and 9 controlled by the control unit 16 through control conductors 8A and 9A control the sequential filling of these containers. More specifically, the container 11 for the crew is filled first and then the container 10 for the passengers is filled. After filling the containers 10, 11, the gas generator 1 remains in a stand-by mode.

In operation, when a sudden drop in the cabin pressure occurs, the gas generator 1 is immediately activated and supplies breathable gas to the mixing unit 14. This gas comes from the low pressure outlet 5 and has an increased concentration of oxygen sufficient to meet requirements. The control unit 16 controls the supply of pure oxygen from the supply tank 10 in response to a pressure representing signal which may be provided in different ways as will be described in more detail below with reference to FIGS. 2, 3 and 4. The oxygen is mixed with the breathable gas in the mixing unit 14 thereby adjusting the oxygen partial pressure in the breathable mixed gas to a value that ensures an adequate supply of oxygen for the passengers. A respective signal from the sensor S3 may be supplied through S3A. The level of the oxygen partial pressure is also dependent upon the cabin pressure which in turn depends on the altitude when depressurization of the cabin occurs. The breathable gas is delivered with a constant mass flow controlled by respective constant mass flow valves 18B through the distribution system 18 to oxygen or breathing masks 18A for the passengers. No ambient air is admixed to this breathable gas in the oxygen or breathing masks 18A of the passengers. However, the breathing masks 13 of the cockpit crew are supplied with oxygen through the pressure reducing valve 12 from the supply container 11. The signal from S1 on S1A is used to make sure that there is always enough oxygen in the tank 11. The supply container 10 which contains the oxygen supply for the passengers serves primarily as a buffer that assures a breathable mixed gas supply for the passengers even when, during the short duration start-up phase of the gas generator 1, an adequate supply of sufficiently concentrated breathable gas is not yet available at the low pressure outlet 5 of the generator 1. The oxygen supply in tank 10 also serves to cover any peak demand for oxygen during the initial phase of an emergency descent of the aircraft. Consequently, the dimensions of the supply container 10 can be comparatively small, since the time durations for start-up and emergency descent to be covered are relatively short. The signal from S2 on S2A is also used to make sure that the tank 10 holds a sufficient oxygen supply for the just described purposes. In FIG. 1 the signal on SA3 is used to monitor the oxygen content or oxygen partial pressure in the breathable gas produced in the gas mixing unit 14.

Figure 2:
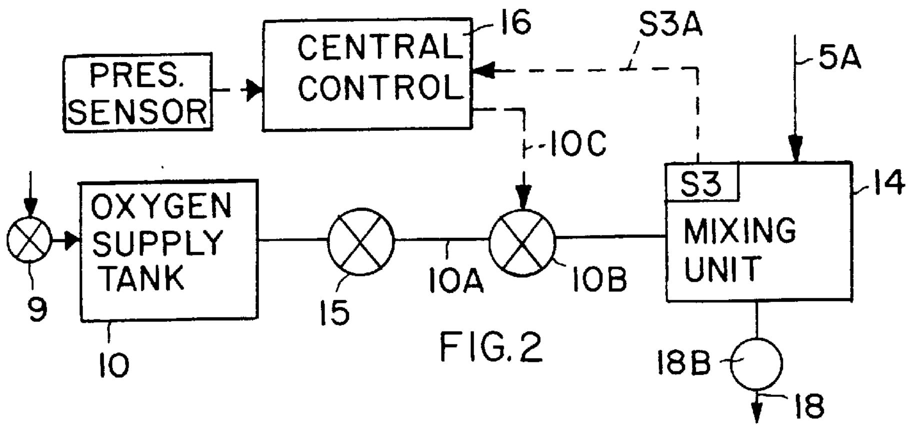
FIG. 2 shows in block form a closed loop control for the oxygen supply into a mixing unit.

FIG. 2 shows a shut-off valve 10B in series with the pressure reduction valve 15 in the gas conductor 10A. The valve 10B is controlled electronically in a closed loop feedback circuit including the sensor S3, the conductor S3A, the central control 16 and the control conductor 10C. The valve 10B, as the flow control valves 8 and 9, are for example solenoid controlled valves. The sensor S3 provides a signal representing the actual partial oxygen pressure in the mixing unit 14. This actual partial oxygen pressure is compared in the control 16 or in the central computer 17 with a rated partial oxygen pressure stored in a memory to provide a control signal on conductor 10C to maintain the partial oxygen pressure at a predefined level meeting official regulations.

Figure 3:
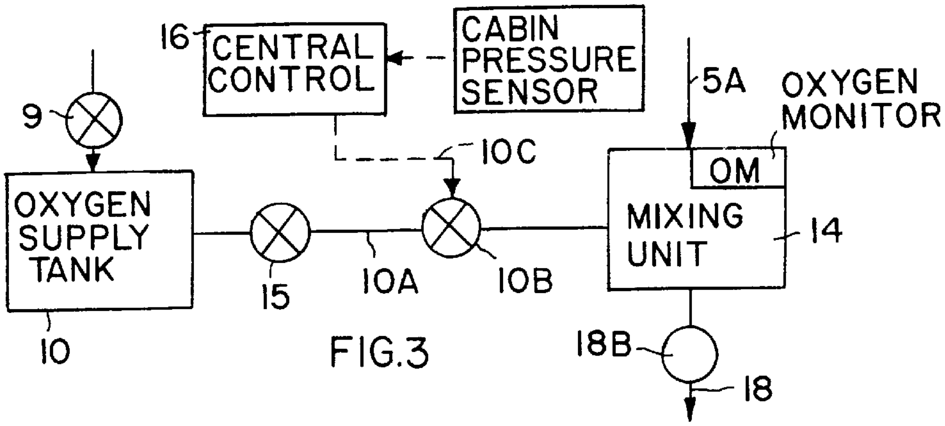
FIGS. 3 and 4 show open loop controls for the oxygen supply into the mixing unit.

FIG. 3 shows an electro-pneumatic control of the flow control valve 10B in response to a cabin pressure drop. An oxygen monitor OM forming part of the mixing unit 14 is provided for monitoring the partial oxygen pressure in the mixing unit 14. The open loop control signal on conductor 10C makes sure that the oxygen partial pressure meets regulation requirements.

Figure 4:
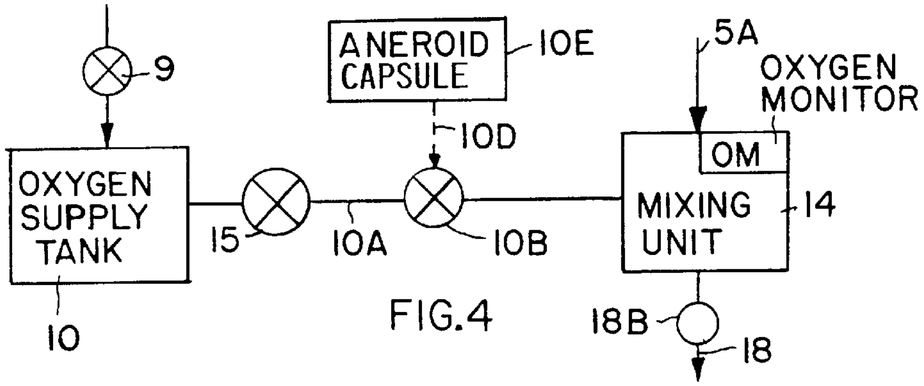

FIG. 4 operates on a pneumatic basis wherein an aneroid capsule operates the valve 10B in response to a cabin pressure drop. Connection 10D is a mechanical connection. Aneroid valves as such are known in the art. An oxygen monitor OM is used as in the embodiment of FIG. 3.

Once an emergency descent is completed, the valve 10B is closed and the oxygen content or oxygen partial pressure in the mixing unit 14 is maintained by the generator 1 through the monitor 7 in response to signals on conductors 7A and 1B.

The oxygen partial pressure could be determined for example by measuring the oxygen concentration in the gas coming from the outlets 5A, 6A and simultaneously calculating the $O_2$-concentration from the pressure, for example in the mixing unit 14. The sensors S3 and S4 could be so-called ZnO-sensors, wherein the oxygen content influences the electrical conductivity of the metal oxide.

The monitor 7 measures and monitors the purity and pressure of the oxygen from the outlet 6 providing pressurized and concentrated oxygen. Respective signals on conductor 7A are processed in the central control unit 16. Respective control signals are then provided to the gas generator 1 and/or to the valves 8, 9 for example to stop filling the oxygen supply tanks if the oxygen coming through the monitor 7 does not have the required purity and to resume filling when the required purity is present.

Although the invention has been described with reference to specific example embodiments, it will be appreciated that it is intended to cover all modifications and equivalents within the scope of the appended claims.

What is claimed is:

1. A method for supplying an oxygen-enriched gas through a distribution system to breathing masks in a cabin of an aircraft, comprising the following steps:

(a) sensing a cabin pressure to provide a cabin pressure representing first control signal, (b) providing a breathable gas in response to said first control signal, (c) mixing said breathable gas with oxygen to produce a mixed oxygen-enriched gas, (d) ascertaining a second control signal representing an actual oxygen partial pressure of said mixed oxygen-enriched gas, (e) controlling said mixing step in response to said second control signal representing said actual oxygen partial pressure of said mixed oxygen-enriched gas to provide said mixed gas with a required or rated oxygen content, and (f) feeding said mixed gas having said required or rated oxygen content to said breathing masks with a constant mass flow.

2. The method of claim 1, comprising generating said breathable gas on board of said aircraft.

3. The method of claim 1, further comprising storing a supply of oxygen on board of said aircraft for said enriching step.

4. The method of claim 1, wherein said step of providing said breathable gas comprises generating said breathable gas from one member of the group of air from the environment and engine tap air.

5. The method of claim 4, further comprising using a molecular sieve for generating said breathable gas.

6. The method of claim 4, further comprising using selectively permeable membranes for generating said breathable gas.

7. The method of claim 1, comprising generating said breathable gas from water by electrolysis.

8. The method of claim 1, further comprising performing at least said controlling of said enriching step in closed loop fashion.

9. An apparatus for supplying an oxygen-enriched gas through an emergency distribution system to breathing masks in a cabin of an aircraft, comprising a pressure sensor for providing a control signal representing cabin pressure, a gas generator (1) connected to be controlled by said first control signal for providing a breathable gas, a gas mixing unit (14) connected to said gas generator (1) for receiving said breathable gas through a first gas conduit (5A), an oxygen supply source (6, 7, 10), a second gas conduit (10A) and a flow control valve in said second gas conduit (10A) connecting said gas mixing unit (14) to said oxygen supply source (10) for feeding oxygen into said mixing unit whereby said breathable gas is mixed with oxygen to produce a mixed oxygen-enriched gas, said flow control valve maintaining an oxygen partial pressure of said mixed gas in said gas mixing unit (14) at a required or rated oxygen content to provide said mixed oxygen-enriched gas, and gas conduits (18) connecting said gas mixing unit (14) to said breathing masks (18A) for feeding said oxygen-enriched gas to said breathing masks.

10. The apparatus of claim 9, wherein said source of oxygen further comprises at least two oxygen storage tanks (10, 11), one tank being provided for a crew, the other tank being connected through said flow control valve to said mixing unit.

11. The apparatus of claim 9, further comprising a central control unit (16), an on-board computer (17) connected to said central control unit (16), said gas generator (1) comprising a control input (1B) connected to said central control unit (16), a low pressure outlet (5), a first gas conduit (5A) connecting said low pressure outlet (5) to said gas mixing unit (14) for supplying said breathable gas into said gas mixing unit (14), said gas generator (1) further comprising a high pressure oxygen outlet (6), said apparatus further comprising an oxygen monitor (7) having an inlet connected to said high pressure oxygen outlet (6) for passing oxygen through said monitor (7), at least two oxygen storage tanks (10, 11), two flow control valves (8, 9) and second gas conduits (7B, 8B) connecting an outlet of said oxygen monitor (7) through said flow control valves (8, 9) to said at least two oxygen storage tanks (10, 11), said flow control valves being connected to said central control unit (16) for opening and closing said two control valves (8, 9) to fill said oxygen storage tanks (10,11), a third gas conduit (10A) connecting one oxygen storage tank (10) of said two oxygen storage tanks to said gas mixing unit (14), a first pressure reducing valve (15) in said third gas conduit (10A) for delivering oxygen to said gas mixing unit (14) at a preset pressure controlled by said first pressure reducing valve (15), a fourth gas conduit (11A) connecting the other oxygen storage tank (11) of said two oxygen storage tanks to crew oxygen masks (13) and a further pressure reduction valve (12) in said fourth gas conduit (11A).

12. The apparatus of claim 11, further comprising a sensor (S3) in said gas mixing unit (14) for sensing an actual oxygen partial pressure, an electrical conductor (S3A) connecting said sensor (S3) to said central control unit (16) for transmitting a signal representing said actual oxygen partial pressure to said central control unit (16) for producing a valve control signal, a third flow control valve (10B) connected in series with said first pressure reducing valve (15) in said third gas conduit (10A), said third flow control valve (10B) being responsive to said valve control signal for feeding oxygen into said gas mixing unit (14) for maintaining a required or rated oxygen partial pressure in said gas mixing unit (14) based on said actual oxygen partial pressure, whereby said third flow control valve (10B) is controlled in a closed loop feedback manner.

13. The apparatus of claim 9, comprising an oxygen outlet (6) and a breathable gas outlet in said gas generator (1), an oxygen monitor (7) connected to said oxygen outlet (6) of said gas generator (1), first and second oxygen storage tanks (10, 11), a third gas conduit (7B) connecting said first and second oxygen storage tanks (11) to said oxygen monitor (7), second and third flow control valves (8, 9) connecting said third gas conduit (7B) to said first and second oxygen storage tanks, control conductors (8A, 9A) connecting said second and third flow control valves (8, 9) to a central control unit (16) for opening and closing said second and third flow control valves (8, 9), a fourth gas conduit (11A) connecting said second oxygen storage tank (11) to oxygen breathing masks (13) for a crew, a pressure reducing valve (12) in said fourth gas conduit (11A), said pressure reducing valve (12) being preadjusted for supplying oxygen to said breathing masks (13) for a crew at a predefined pressure.

14. The apparatus of claim 13, further comprising sensors (S1, S2) in said first and second oxygen storage tanks (10, 11) for sensing an oxygen pressure in said first and second oxygen storage tanks (10, 11), and electrical conductors (S1A, S2A) connecting said sensors (S1, S2) to said central control unit (16), said control conductors (8A, 9A) providing said second and third flow control valves (8, 9) with a control signal from said central control unit (16) based on oxygen pressure signals from said first and second oxygen storage tanks (10, 11).

15. The apparatus of claim 9, further comprising a compressor (2) and a gas cooler (3) connected in series with each other, said gas cooler having an outlet connected to an inlet (1A) of said gas generator (1), said compressor (2) having an inlet for taking in outside air.

16. The apparatus of claim 9, further comprising a cooler (3) having an inlet connected to receive engine tap air and an outlet connected to said gas generator (1).

17. The apparatus of claim 9, further comprising a cooler (3) having a ram air inlet to collect outside air and an outlet connected to said gas generator (1).

18. The apparatus of claim 9, wherein said gas generator comprises a fresh water inlet and a water electrolysis device for producing breathable gas from water.

19. The apparatus of claim 9, wherein said gas generator (1) comprises an oxygen outlet (6), said apparatus further comprising an oxygen monitor (7) having an inlet connected to said oxygen outlet of said gas generator (1), a sensor (S4) in said oxygen monitor connected through an electrical conductor (7A) to a central control unit (16) for providing oxygen information to said central control unit (16).

20. A method for supplying an oxygen-enriched gas through a distribution system to breathing masks in a cabin of an aircraft, comprising the following steps:

(a) sensing a pressure to provide a pressure representing control signal, (b) providing a breathable gas in response to said control signal, (c) mixing said breathable gas with oxygen for producing a mixed oxygen-enriched gas in response to said control signal to provide said mixed gas with a required oxygen content, and (d) feeding said mixed gas having said required oxygen content with a constant mass flow to said breathing masks.

21. The method of claim 20, wherein said step of sensing a pressure comprises sensing a cabin pressure to generate said pressure representing control signal as a signal representing a cabin pressure drop.

22. The method of claim 20, further comprising producing a further signal representing a partial oxygen pressure in said mixed gas, comparing said actual partial oxygen pressure with a rated partial oxygen pressure to provide an oxygen supply control signal, and controlling said partial oxygen pressure in said mixed gas in closed loop fashion in response to said oxygen supply control signal.

* * * * *